United States Patent [19]

Naylor

[11] 4,414,212

[45] Nov. 8, 1983

[54] METHOD OF TREATMENT OF PRE-MENSTRUAL SYNDROME

[75] Inventor: Graham J. Naylor, Lugate, Lucklawhill Balmiallo, St. Andrews, Fife, Scotland, KY16 OBQ

[73] Assignees: Graham J. Naylor; Pamela H. Naylor, both of Andrews, Scotland

[21] Appl. No.: 354,065

[22] Filed: Mar. 2, 1982

[51] Int. Cl.³ ............... A61K 31/54; A61K 31/365; A61K 31/195; A61K 37/00
[52] U.S. Cl. .............................. 424/247; 424/280; 424/319; 424/177
[58] Field of Search ............... 424/319, 280, 247, 177

[56] References Cited

FOREIGN PATENT DOCUMENTS

| | | | |
|---|---|---|---|
| 2455203 | 5/1975 | Fed. Rep. of Germany | 424/251 |
| 857582 | 3/1962 | France | 424/251 |
| 1054698 | 1/1967 | United Kingdom | 424/251 |

OTHER PUBLICATIONS

*Biochimica et Biophysica Acta*, "Glutathione Reduces Cytoplasmic Vanadate Mechanism and Physiological Implications," vol. 629, 1980, pp. 95–106.
*Gazette Medicale de France*, "Vitamin C and Dysmenorrhea", vol. 67, 1960, pp. 1111–1112.
*The Healing Factor*–"Vitamin C against Disease", Pregnancy, Stone,1972, pp. 186–192, 246–250.
*Biochem. Journal*, vol. 128(4), Jul. 1972, p.139p.
Chemical Abstracts 91:86268g, 91:86363j.

*Primary Examiner*—Stanley J. Friedman
*Assistant Examiner*—F. Abramson
*Attorney, Agent, or Firm*—Murray & Whisenhunt

[57] ABSTRACT

This invention relates to a method of treatment and/or prophylaxis of pre-menstrual syndrome comprising the administration of a therapeutically or prophylactically effective dosage of at least one of ascorbic acid, EDTA, glutathione, and a compound of Formula I

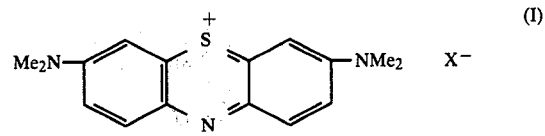

wherein X is a physiologically acceptable anion, and bioprecursors thereof, to a patient suffering from pre-menstrual syndrome.

10 Claims, No Drawings

METHOD OF TREATMENT OF PRE-MENSTRUAL SYNDROME

This invention relates to the treatment of pre-menstrual syndrome.

At the present time there is an increasing awareness of the effects of pre-menstrual syndrome which result in considerable problems both for those members of society affected by the more acure forms of this phenomenon and for those others who come into contact with the sufferers.

Present day methods for the control and management of these conditions often involve substantial medical care.

One known treatment for pre-menstrual syndrome comprises the administration of a diuretic during the second half of the menstrual cycle. This sometimes relieves some of the physical symptoms e.g. the sense of distension, but does little for the mental symptoms. None of the known treatments are very effective for pre-menstrual syndrome.

The present invention provides a method of treatment and/or prophylaxis of pre-menstrual syndrome comprising the administration of a therapeutically or prophylactically effective dosage of at least one of ascorbic acid, EDTA, glutathione; and physiologically acceptable salts and esters thereof, and a compound of formula I

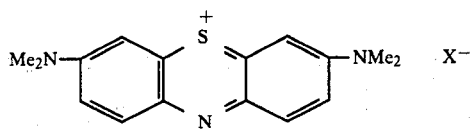

wherein X is a physiologically acceptable anion, and bioprecursors thereof, to a patient suffering from pre-menstrual syndrome.

Preferably there is used a compound of formula I in which the anion is a halide anion especially chloride. In the latter case the compound of formula I is known as methylene blue or 3,7-bisdimethylaminophenothiazine hydrochloride having the chemical formula $C_{16}H_{18}ClN_3S$. Other suitable anions which may be mentioned include sulphate, nitrate, citrate, carbonate and fumarate.

For the avoidance of doubt the compound referred to as EDTA is ethylenediaminetetra-acetic acid and glutathione is the compound having the name:

γ-L-glutamyl-L-cysteinylglycine (oxidised or reduced form) and the chemical formula

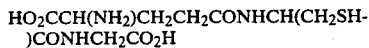

(in the case of the reduced form).

As well as being substantially free from the above-mentioned disadvantages of prior art methods to a greater or lesser extent, the present invention has additional advantages in that methylene blue, ascorbic acid, glutathione and EDTA appear to be more effective and considerably cheaper than other treatments.

As already indicated the present invention extends to the administration of bioprecursors of ascorbic acid, EDTA, glutathione, and a compound of formula I, namely substances which are readily converted in the human body upon administration into said first mentiond compounds.

The preparation of the active compounds including those of formula I in particular of methylene blue are well known from the literature. Particular desired salts, esters or precursors can be readily produced by standard procedures such as metathetical reactions.

The inventor has also found that methylene blue, also known as methylthionine chloride, has significant in vitro and in vivo activity in the reversal of Na-K ATPase inhibition caused in the body by, in particular, vanadate ions. It is believed that this is achieved by the reduction of vanadate ($V^{5+}$) ions to vanadyl ($V^{4+}$) ions. Whilst not restricting the scope of the present invention in any way it is believed by the inventor that the effectiveness of the method of the present invention is by means of the reversal of the Na-K ATPase inhibition in the body by vanadate ions.

The active compounds of the invention are usually administered in the form of a pharmaceutical formulation comprising ascorbic acid physiologically acceptable salt or ester thereof, EDTA, glutathione, physiologically acceptable salt or ester thereof, or the compound of formula I, or a bioprecursor thereof together with a pharmaceutically acceptable carrier therefor.

The carrier must be "acceptable" in the sense of being compatible with the other ingredients of the formulation and not deleterious to the patient. Such carriers may be solid, liquid or gaseous materials suitable for the purpose of administering the medicament by the desired route.

These pharmaceutical compositions may be administered orally or parenterally (including subcutaneous, intramuscular and intravenous injection) or as a suppository or pessary. In general the compositions are administered orally or parenterally. The words formulation and composition are used synonymously herein.

For parenteral administration the active compound may be presented in sterile solutions or suspensions in aqueous or oleaginous vehicles, which may also contain preservatives and material for rendering the solution or suspension isotonic with the blood of the patient. The formulations are conveniently presented in unit-dose or multi-dose sealed containers.

For oral administration the pharmaceutical compositions may be formulated as a draught in water or in a syrup, in capsules, cachets, boluses or tablets, as an aqueous or oleaginous solution or suspension or in suspension in a syrup, such suspensions optionally including suspending agents, or as an oil-in-water or water-in-oil emulsion. Flavouring, sweetening, preserving, thickening or emulsifying agents may also be included in the formulation.

Tablets may contain the active compound as a powder or granules optionally mixed with binders, lubricants, inert diluents or surface-active or dispersing agents and may be formed by compression or by moulding in inert liquid diluent. Such tablets may be scored and/or coated.

Capsules and cachets may contain the active compound alone or in admixture with one or more other ingredients. Capsules may also contain the active compound in aqueous or oleaginous solution suspension or emulsion optionally in association with other ingredients. For administration as a suppository or pessary the active compound may be presented in admixture with a suitable carrier such as cocoa butter and other material commonly used in the art, and are conveniently shaped by moulding. For administration in discrete unit dosage forms such as tablets, capsules, suppositories and pessaries as described above, the active compound is preferably present at from 1 mg to 400 mg, most preferably from 25 mg to 400 mg, per tablet, capsule, suppository or pessary in the case of methylene blue and from 25 mg to 1 g, most preferably 200 mg to 1 g for ascorbic acid and glutathione and EDTA.

All the above formulations may be produced by standard processes comprising bringing the active compound into association with one or more pharmaceutically acceptable carriers.

The required effective dosage of the compound or agent of the invention will of course depend on various factors such as the activity of the individual compound, the depth, and severity of the illness, and the responsiveness of the individual patient to the treatment regimen used. In general though the compound or agent will be administered at a dosage in the range of from 0.1 mg to 2 g per kg body weight of the patient per day, preferably from 0.2 to 8 mg/kg in the case of methylene blue, from 5 mg to 2 g per kg bodyweight of the patient per day in the case of ascorbic acid, and from 0.2 to 500 mg per kg bodyweight per day, preferably from 10 to 100 mg per kg of glutathione and from 5 mg to 2 g per kg bodyweight of the patient per day in the case of EDTA. Advantageously the dosage is administered in two or more equal portions at approximately equal intervals.

Further preferred features of the invention will appear from the following examples.

EXAMPLE 1

A female patient aged 28 years old had for several years suffered from the pre-menstrual syndrome. This had manifested itself as irritability, depression of mood, disturbed sleep, loss of appetite but accompanied by weight gain in the second half of her menstrual cycle. She had failed to respond to a variety of treatments e.g. antidepressants, tranquillizers, oral contraceptives etc. She was treated with methylene blue, 150 mg twice daily, commencing on the twelfth day of her menstrual cycle. Her pre-menstrual syndrome (including the weight change) virtually disappeared except for the 24 hours before menstruation commenced.

EXAMPLE 2

A double blind trial of ascorbic acid and placebo was carried out in 7 women who suffered from the pre-menstrual syndrome. The patients received 3 g per day of ascorbic acid for two cycles and placebo for two cycles (or vice versa). All seven women judged themselves to be better on the ascorbic acid than when on placebo.

What is claimed is:

1. A method of treatment of pre-menstrual syndrome in a female patient suffering from pre-menstrual syndrome, said method comprising the step of administering to said patient a therapeutically effective dosage of at least one compound selected from the group consisting of ascorbic acid, physiologically acceptable salts and esters thereof, EDTA, glutathione, physiologically acceptable salts and esters thereof, and a compound of Formula I

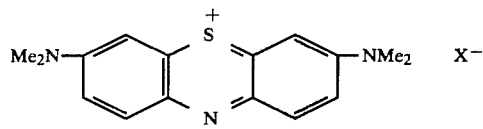

wherein X is a physiologically acceptable anion, and bioprecursors thereof.

2. A method according to claim 1 wherein X is a halide anion.
3. A method according to claim 2 wherein the compound is methylene blue.
4. A method according to claim 3 wherein methylene blue is administered at a dosage rate of from 0.2 to 8 mg per kg bodyweight of the patient per day.
5. A method of prophylaxis of pre-menstrual syndrome in a female patient who has suffered from pre-menstrual syndrome, said method comprising the step of administering to said patient a prophylactically effective dosage of at least one compound selected from the group consisting of ascorbic acid, physiologically acceptable salts and esters thereof, EDTA, glutathione, physiologically acceptable salts and esters thereof, and a compound of Formula I $$Me_2N\text{—}\underset{N}{\overset{+}{S}}\text{—}NMe_2 \quad X^- \qquad (I)$$

wherein X is a physiologically acceptable anion, and bioprecursors thereof.

6. A method according to claim 5 wherein X is a halide anion.
7. A method according to claim 6 wherein the compound is methylene blue.
8. A method according to claim 7 wherein methylene blue is administered at a dosage rate of from 0.2 to 8 mg per kg bodyweight of the patient per day.
9. A method of treatment of pre-menstrual syndrome in a female patient suffering from pre-menstrual syndrome, said method comprising the step of administering to said patient a vanadate ion induced Na-K ATPase inhibition reversing effective dosage of a vanadate ion induced Na-K ATPase inhibition reversing agent selected from the group consisting of ascorbic acid, physiologically acceptable salts and esters thereof, EDTA, glutathione, physiologically acceptable salts and esters thereof, and a compound of Formula I $$Me_2N\text{—}\underset{N}{\overset{+}{S}}\text{—}NMe_2 \quad X^- \qquad (I)$$

wherein X is a physiological acceptable anion, and bioprecursors thereof.

10. A method of prophylaxis of pre-menstrual syndrome in a female patient who has suffered from pre-menstrual syndrome, said method comprising the step of administering to said patient a vanadate ion induced Na-K ATPase inhibition reversing effective dosage of a vanadate ion induced Na-K ATPase inhibition reversing agent selected from the group consisting of ascorbic acid, physiologically acceptable salts and esters thereof,
EDTA, glutathione, physiologically acceptable salts and esters thereof, and a compound of Formula I
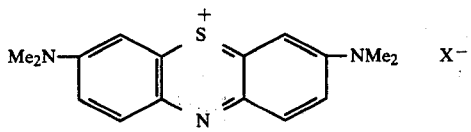
wherein X is a physiologically acceptable anion, and bioprecursors thereof.
* * * * *